United States Patent [19]
Smith et al.

[11] Patent Number: 5,545,304
[45] Date of Patent: Aug. 13, 1996

[54] ION CURRENT DETECTOR FOR HIGH PRESSURE ION SOURCES FOR MONITORING SEPARATIONS

[75] Inventors: Richard D. Smith; Jon H. Wahl; Steven A. Hofstadler, all of Richland, Wash.

[73] Assignee: Battelle Memorial Institute, Richland, Wash.

[21] Appl. No.: 441,319

[22] Filed: May 15, 1995

[51] Int. Cl.⁶ .......................... H01J 49/04; B01D 59/44; G01N 27/26; G01N 27/447
[52] U.S. Cl. .......................... 204/603; 204/452; 204/601; 250/288; 73/61.58
[58] Field of Search .................. 204/299 R, 180.1; 250/288; 324/71.3, 464, 465, 466, 467, 468, 469, 470; 73/61.58

[56] References Cited

U.S. PATENT DOCUMENTS

| | | | |
|---|---|---|---|
| 4,455,532 | 6/1984 | Gregory et al. | 324/71.3 X |
| 4,842,701 | 6/1989 | Smith et al. | 204/180.1 |
| 4,885,076 | 12/1989 | Smith et al. | 204/180.1 X |
| 4,994,165 | 2/1991 | Lee et al. | 204/180.1 X |
| 5,126,023 | 6/1992 | Huang et al. | 204/180.1 |
| 5,170,053 | 12/1992 | Hail et al. | 204/180.1 X |
| 5,244,560 | 9/1993 | Kuhr | 204/299 R |
| 5,298,139 | 3/1994 | Huang et al. | 204/299 R |

*Primary Examiner*—John Niebling
*Assistant Examiner*—John S. Starsiak, Jr.
*Attorney, Agent, or Firm*—Johnnie R. Hynson

[57] ABSTRACT

The present invention relates generally to any application involving the monitoring of signal arising from ions produced by electrospray or other high pressure (>100 torr) ion sources. The present invention relates specifically to an apparatus and method for the detection of ions emitted from a capillary electrophoresis (CE) system, liquid chromatography, or other small-scale separation methods. And further, the invention provides a very simple diagnostic as to the quality of the separation and the operation of an electrospray source.

9 Claims, 6 Drawing Sheets

ION CURRENT DETECTOR FOR HIGH PRESSURE ION SOURCES FOR MONITORING SEPARATIONS

This invention was made with Government support under Contract DE-AC06-76RLO 1830, awarded by the U.S. Department of Energy. The Government has certain rights in the invention.

FIELD OF THE INVENTION

The present invention relates generally to any application involving the monitoring of signal arising from ions produced by electrospray or other high pressure (>100 torr) ion sources. The present invention relates specifically to an apparatus and method for the detection of ions emitted from a capillary electrophoresis (CE) system, liquid chromatography, or other small-scale separation-methods. And further, the invention provides a very simple diagnostic as to the quality of the separation and the operation of an electrospray source.

BACKGROUND OF THE INVENTION

Separation of molecular constituents is necessary when only small amounts of the sample are available. Under these circumstances the other constituents in the sample can interfere with the analysis.

It is therefore an object of the instant invention to be able to provide real time read out of the degree of ion separation.

Finally, there is a need for general, non-selective detectors with high sensitivity.

The use of MS shutters is known in the art. However, these applications use the shutter in an open or shut configuration. Also, changing operation from a shutter configuration to an ion collector requires manual changes in the detection system.

SUMMARY OF THE INVENTION

The instant invention relates to a method and apparatus for the detection of ions; more particularly, the instant invention relates to the real time detection of ions from molecular or chemical separators. It is relevant to molecular separations using capillary electrophoresis or liquid chromatography (LC), but it is also applicable to analysis of any liquid phase process that may be monitored from a liquid stream delivered through a small diameter capillary.

The detection scheme of the instant invention has several inherent features which may be advantageous over conventional detection schemes. The instant invention meets the need for a general, non-selective detector with high sensitivity. The detection scheme is based upon the separation of ions, their mass during transport from a high pressure ion formation region (>100 torr), and into a low pressure region where the more collimated nature of the more massive ions allows their selective detection. The instant invention is particularly relevant to atmospheric pressure electrospray ion sources, and is applicable to any high pressure ion source.

Applicability to Very Small Capillaries

UV (ultra-violet) detectors are based on measuring a difference in absorption between the running buffer and the analyte zones. As the absorptivity is directly dependent on path length, smaller i.d. capillaries are inherently more difficult to work with. The ion current detection scheme described here is highly effective with small i.d. capillaries as sensitivity is optimized and the generation of an electrospray plume is enhanced with small capillaries. Therefore, with efficiently generated electrospray plumes, this invention offers high sensitivity when used with small i.d. CZE or Micro LC capillaries.

Applicability to Non-UV Compatible Buffer Systems

Instances in which the running buffer or LC mobile phase is not UV compatible (e.g. strongly absorbs UV wavelengths) are not problematic to the ion current detection scheme described herein as the detection scheme is based solely on the discrimination of analyte ions from buffer ions in the electrospray ionization source.

Complimentary to Concurrent Mass Spectral Detection

When used in tandem with mass spectrometric detection, the ion current detection scheme provides an accurate measure of when the analyte is entering the mass spectrometer.

Cost/Simplicity

When used with mass spectrometry, only very minor (or no) instrument modifications are necessary to permit the utilization of the ion current detection scheme. When used as a stand alone detection scheme, such a detector can be easily assembled from standard vacuum hardware at modest expense. It is likely that ion current measurements directly on the skimmer cone(s), or other collimating device used to separate the more massive ions from the lighter ions, could provide similar ion current profiles after incorporation of a collimating aperture.

Sensitivity

Results suggest that the ion current detection scheme may provide sensitivity which rivals that of many conventional detection schemes.

Mass Spectrometry Shutters

The use of MS and shutters are known in the art, however, the use of the operating arm as an ion collector is not. Nor is the use of the operating arm/ion collector in a partially open position to enable the simultaneous use of an MS unit and the ion collector via the MS connection. This feature allows simultaneous readout of real time ion detection and data received by the MS unit.

DESCRIPTION OF THE PREFERRED EMBODIMENT(S)

General Description

Figure 1A:
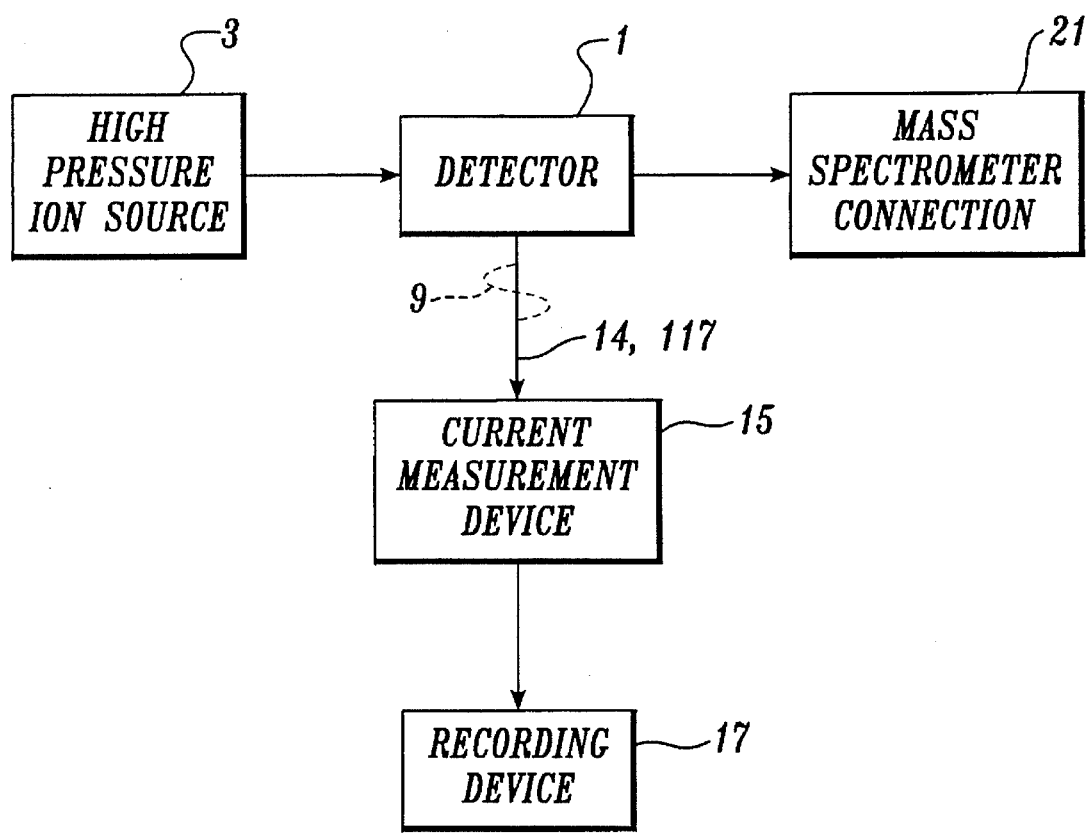
FIG. 1a is a block diagram illustrating the use of the ion detector with respect to an ammeter and a mass spectrometer.
Figure 1B:
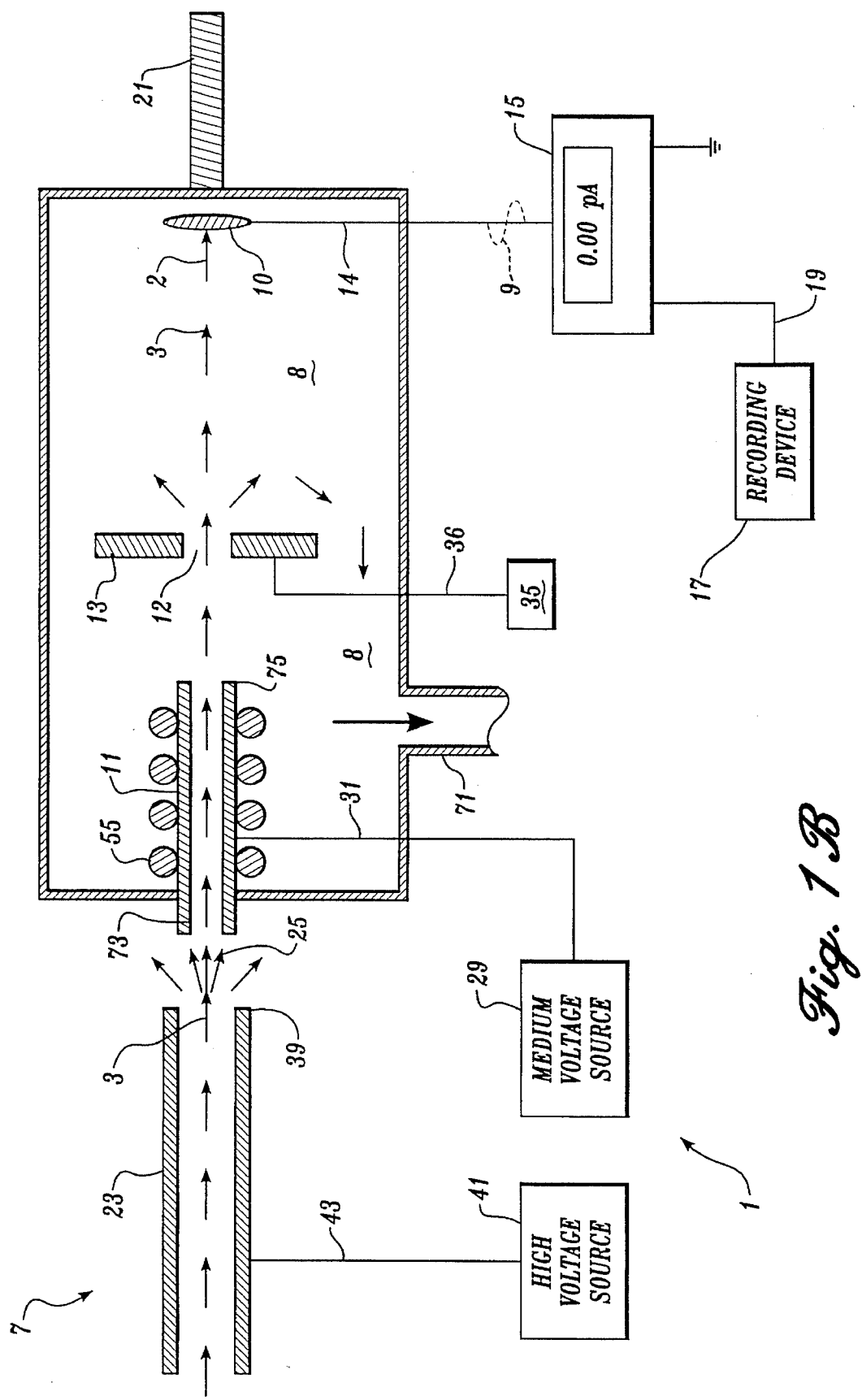
FIG. 1b is a schematic representation of the instant invention.

Referring now to FIGS. 1a and 1b, the instant invention is an ion detector 1 for use with several different types of separation methods. However, the most common applications will be in the detection of ions 3, which are preferably large organic ions, from any high pressure ion source 5. The high pressure ion source 5 will typically be either a capillary electrophoresis unit (CE) 7 or a liquid chromograph unit (not shown). The output of the CE unit 7 is directed to the ion detector 1 and ionized by electrospray ionization. The ions 3 are detected by a signal 9 that is produced when an ion 3 strikes the ion collector plate 10. To reach the collector plate 10 the ions 3 must flow through a desolvation capillary 11 and then through a plate aperture 12 in a collimating plate 13. When an ion 3 strikes the ion collector plate 10, a signal 9 is registered by a current measurement device 15 (also ammeter) and is then transmitted to a recording device 17.

In the practice of the invention the signal 9 will be typically sent to an ammeter or current measurement device 15 via an ammeter lead 14, and from there to a chart type recording device 17 via a recording lead 19. The recording device 17 will typically be an ammeter which is a very sensitive measurement device 15, i.e. can detect currents less than $10^{-11}$ amps.

An advantage of the instant invention is that it can be used simultaneously with a mass spectrometer through a mass spectrometer connection 21. The particular configuration of the mass spectrometer connection 21 is not germane to the instant invention.

Detection Scheme

Now referring to FIG. 1b the ions 3 traveling through the CE capillary 23 are sprayed in an electrospray plume 25 toward the ion detector 1 and a portion thereof enters a desolvation capillary 11 that is connected to a medium voltage source 29. The ions 3 then pass through a collimating aperture 12, in a collimating plate 13 that is connected to a voltage source 35 via a lead 36, and strike an ion collector plate 10.

The heated desolvation capillary 11, collimating plate aperture 12, and ion collector plate 10 are located within a vacuum chamber 8.

The ions 3 that strike an ion collector plate 10 transmit signals 9 to an ammeter 15 to which is attached a recording device 17 for monitoring and recording the detection signal 9.

Figure 2:
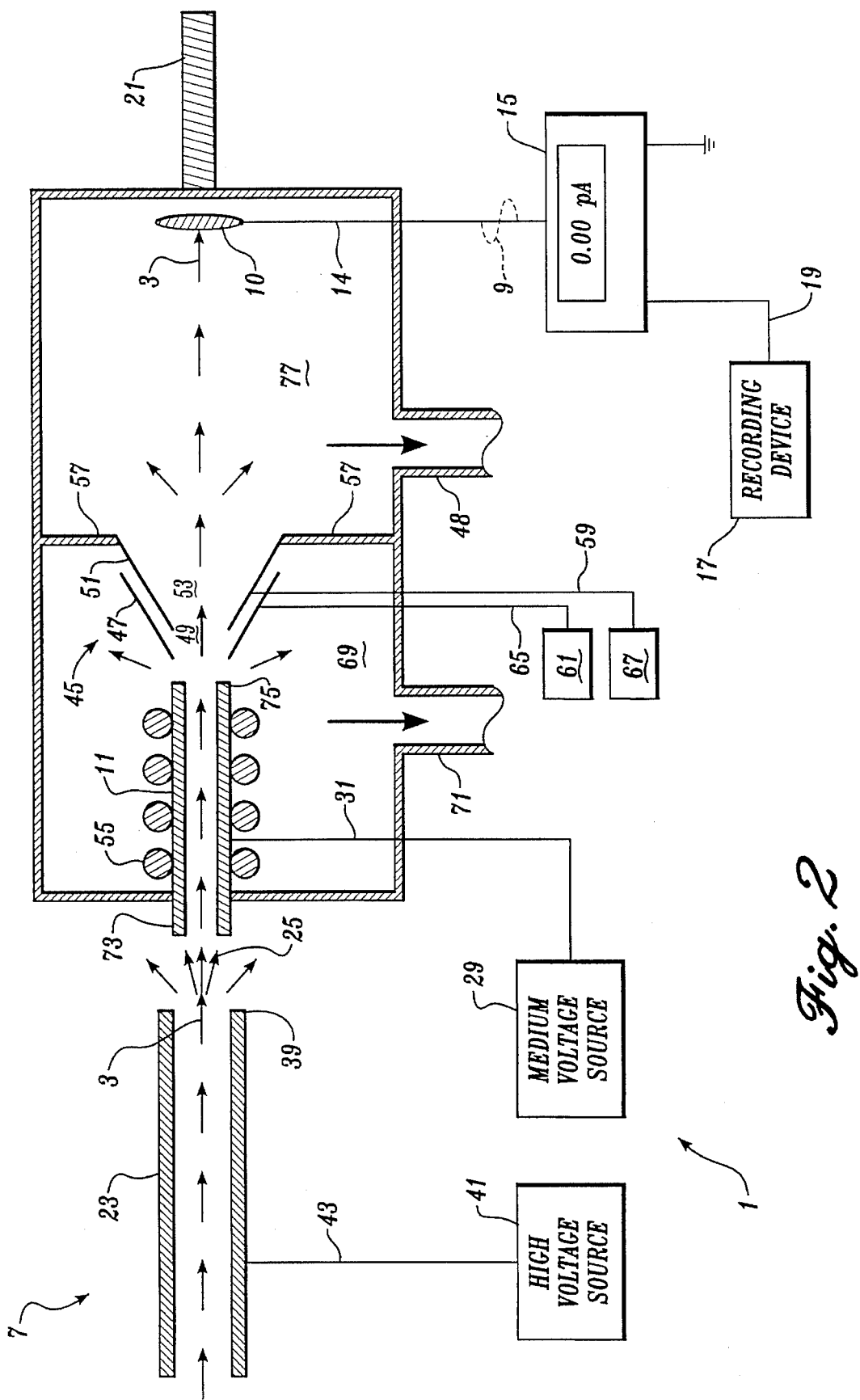
FIG. 2 is a schematic representation of a single skimmer embodiment of the ion detector.

Now referring to FIG. 2, the ions 3 traveling through the CE Capillary 23 are sprayed in an electrospray plume 25 toward the ion detector 1 and enter a desolvation capillary 11. The CE Capillary 23 is typically from 10–100 μm in inner diameter; the CE Capillary terminus 39 is connected to a high voltage source 41 of approximately 3500 VDC via a high voltage lead 43, which establishes the electrospray plume 25.

Use of a Lens Assembly In the Detection Scheme

Flow Path With Skimmer Assembly

Still referring to FIG. 2, from the desolvation capillary 11 the ions 3 are transmitted through at least one skimmer assembly 45 consisting of a first skimmer cone 47 (having a cone aperture 49 that is typically in the center portion of the cone) and a first lens 51 (also having a lens aperture 53 that is typically in the center portion of the cone) before striking an ion collector plate 10. The ions 3 that strike an ion collector plate 10 produce signals 9 to an ammeter 15, typically a pico ammeter 15, to which is attached a recording device 17 for monitoring and recording the detection signal 9. The recording device 17 is typically a chart recorder.

The desolvation capillary 11, which is typically from 300 μm to 1 mm i.d., is heated by means of resistive heating leads 55. A desolvation channel (not shown) can also serve the same function as a desolvation capillary 11. The purpose of the channel or capillary is to serve a region that removes residual solvent and collimates the more massive ions 3. Heating can also be accomplished by means of passing current through the desolvation capillary 11 itself. Heating the capillary is generally desirous because it greatly accelerates the rate of droplet desolvation and enhances the yield of solvent free ions which are characteristic of the analyte. The desolvation capillary 11 is connected to a medium voltage source 29 which biases the desolvation capillary 11 to receive the ions 3 from the CE Capillary 23 and allows passage through the skimmer assembly 45. The typical voltage of the medium voltage source 29 is approximately 100–300 VDC and is applied via a medium voltage lead 31. It should be recognized that only the relative voltages are important. The same motive effects on the ions 3 can be achieved by a biasing scheme that is relative to ground potential.

First Skimmer Assembly Arrangement

The first lens 51 will be biased to about 22.3 VDC by connection via a first lens lead 59 which is connected to a first lens voltage source 61. Likewise, the first skimmer cone 47 will be biased to about 55.7 VDC by connection via a first skimmer lead 65 to a first lens voltage source 67. The ions 3 stream passes through the first skimmer cone then through the first lens 51.

Multiple Vacuum Chambers

As illustrated in FIG. 2, the desolvation capillary 11 is located within a first vacuum chamber 69. Vacuum is created in the first vacuum chamber 69 by means of a vacuum pump (not shown) which is connected to the vacuum chamber 69 via a first vacuum line 71. The resulting pressure difference from the receiving tip 73 across the desolvation capillary 11 produces a supersonic expansion at the low pressure end 75 of the desolvation capillary. Ion transmission is improved in the lower pressure environment as scattering due to ion collisions with other background constituents is minimized. This is due to neutralization from ion-constituent molecule reactions.

Figure 3:
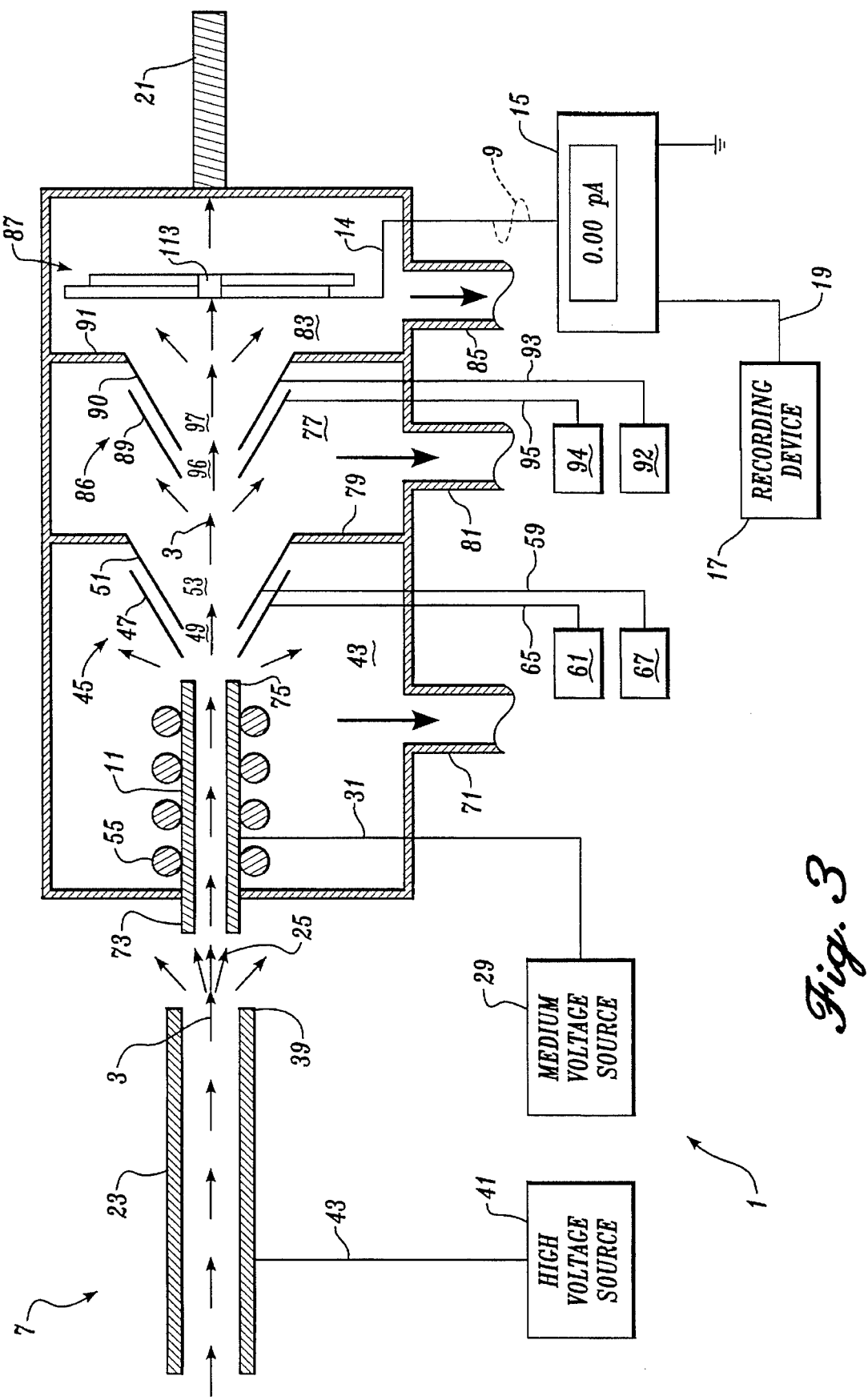
FIG. 3 is a schematic representation of a multiple skimmer embodiment of the ion detector.

Referring now to FIG. 3 the first skimmer assembly 45 separates the ion detector 1 into a first vacuum chamber 69 and a second vacuum chamber 77. A wall 79, that also acts as support for the first skimmer assembly 45, is the means of separation of the chambers 69,79.

A second vacuum line 81 is required for the second vacuum chamber 77. Additional vacuum lines would be required for each of additional chambers that are required by the additional skimmer assemblies being placed in the ion flow path. However, a single vacuum pump (not shown) could be used.

Subsequent Skimmer Assemblies

Referring again to FIG. 3, a plurality of skimmer assemblies 45 can be used. The number of skimmer assemblies 45 used is dependant upon the degree of differential pumping that is desired for the ions 3 passing through the ion detector 1.

It should be noted that a final vacuum chamber 83 should be used around the ion collector plate 10. A vacuum will likewise be drawn in final vacuum chamber 83 via a vacuum line 85. The embodiment is shown in which a shutter assembly 87 is used as an ion collector plate 10.

The second skimmer assembly 86 consists of a second skimmer cone 89, a second lens 90, a second skimmer separating wall 91, a second lens power supply 92, and a second lens power supply lead 93. The second skimmer cone 89 would be biased at approximately 56 VDC by connection via a second cone lead 95 to the second skimmer cone power supply 94. A voltage setting 0 VDC for the second skimmer cone power supply 94 has been used with success in experimental trials of the instant invention. A second cone, or second lens 90 is located within and behind the second skimmer cone 89 in the direction of the ion 3 flow. The second lens 91 is biased at approximately 59 VDC by connection via a second lens lead 93 to the second lens power supply 92.

The second skimmer lens 90 has a second lens aperture 97 and the second skimmer cone 89 has a second cone aperture 96 through which the ions 3 pass.

The lens assembly and the skimmer cone biasing schemes are used to maximize transmission of charged analyte molecules 3 through the electrospray source to the ion current detector plate 10. It is likely that the focal properties of the lens assemblies augments the (desirable) discrimination against low mass buffer ions.

Shutter as an Ion Collector Plate

The ions 3 impinge upon an ion collector plate 10 after leaving the skimmer assemblies. When the ions 3 strike the ion collector plate 10, a signal 9 is generated that is read in real time by the pico-ammeter 15. The event is recorded by a chart recorder 17, or other recording device 17, at the same time. As previously noted, an advantage of the instant invention is that when used with mass spectrometry detection events, the acquired spectra and the total ion profile can be read in real time.

As with the other embodiments when the ion collector plate 10 is a shutter assembly 87, the assembly is located within a final vacuum chamber 83 that is also connected to a vacuum pump via a final vacuum line 85.

Figure 4B:
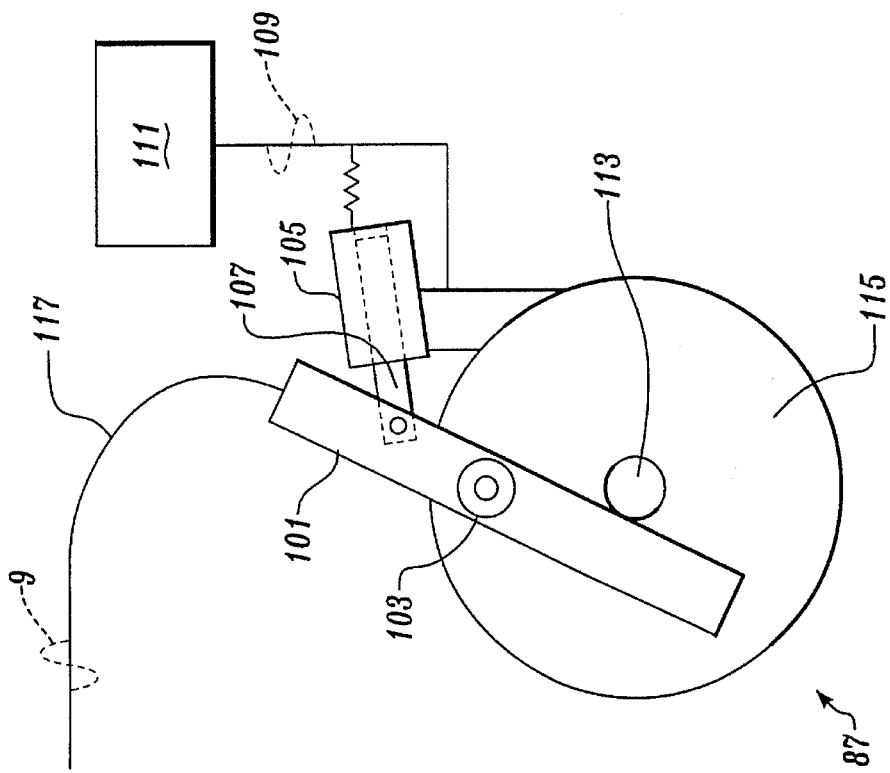
FIG. 4b is a schematic representation of the shutter assembly with the operating arm moved to a position where the shutter aperture is open.
Figure 4A:
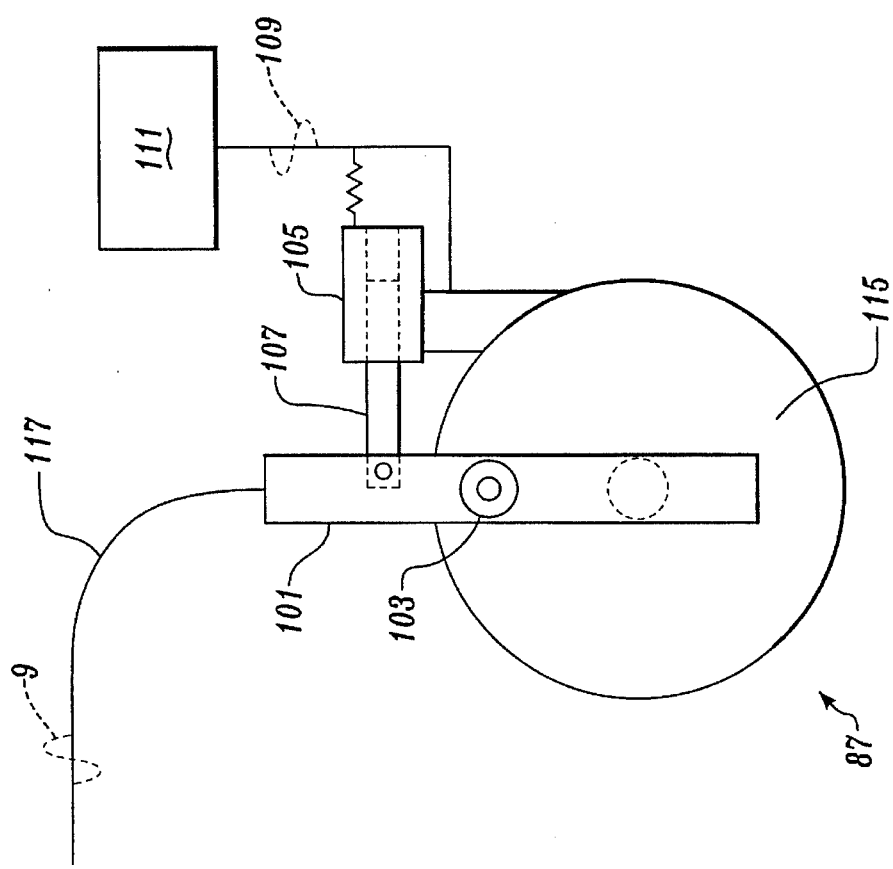
FIG. 4a is a schematic representation of the shutter assembly with the operating arm covering the shutter aperture.

Referring now to FIGS. 4*a* and 4*b*, the ion collecting portion of the shutter assembly 87 is an operating arm 101 that turns on a pivot point 103. The operating arm is remotely operated by means of a solenoid 105 that moves a connecting link 107 that is attached to the operating arm 101. A remote signal 109, generated by a control unit 111, causes the solenoid 105 to activate which causes the connecting link 107 to move, and that in turn causes the operating arm 101 to move. The movement of the operating arm 101 causes a shutter aperture 113 to be uncovered, thereby allowing the ion stream 3 to enter whichever mass spectrometry (MS) connection 21 has been installed. The use of MS and shutters are known in the art; however, the use of the operating arm 101 as an ion collector is not known. Also not known to the art is the use of the operating arm/ion collector 101,10 in a partially open position to enable the simultaneous use of an MS unit and the ion collector via the MS connection 21. This feature allows simultaneous readout of real time ion detection and data received by the MS unit.

The connecting link 107 will typically be connected to the operation arm 101 by means of a pivot point 103. The shutter body 115 can also be used as a wall or it can stand freely within the final vacuum chamber 83. The operating arm 101 and the solenoid 105 will typically be mounted on the shutter body 115.

As in the ion collector plate 10 discussed above, the operation arm 101 is also connected via a shutter ammeter lead 117 to the pico-ammeter 15. From that point the signals 9 are analyzed.

Experimental Results

A peptide/protein mixture was injected into a capillary electrophoresis (CE) instrument 7 and, following electrophoretic separation in a 10 mM acetic acid running buffer, the components were detected using the instant invention. The peptide/protein test mixture used in this example was composed of somatostatin (MW=1,638 Da), ubiquitin (MW=8,565 Da), α-lactalbumin (MW=14,175 Da), lysozyme (MW=14,306 Da), myoglobin (MW=16,951 Da), and carbonic anhydrase I (MW=28,802 Da), each at 50 μM in doubly-distilled deionized water. During the CE unit 7 separation a constant electrospray plume 25 (consisting primarily of the 10 mM HOAc running buffer) is maintained between the terminus of the CE capillary 39 and the desolvating capillary receiving tip 18 by the application of a static 3–4 kV voltage offset relative to the desolvating capillary. As each component elutes from the terminus of the CE capillary 39, it is ionized by electrospray ionization. During the elution of an analyte zone the electrospray current measured at the emitter (typically ~0.1 μA) does not change appreciably. The resulting beam of charged analyte molecules, when impinging on the detection electrode 29, creates a measurable current (typically 10–100 pA) which, when plotted against time, provides a dynamic record of the elution profile for the analyte mixture.

Figure 5:
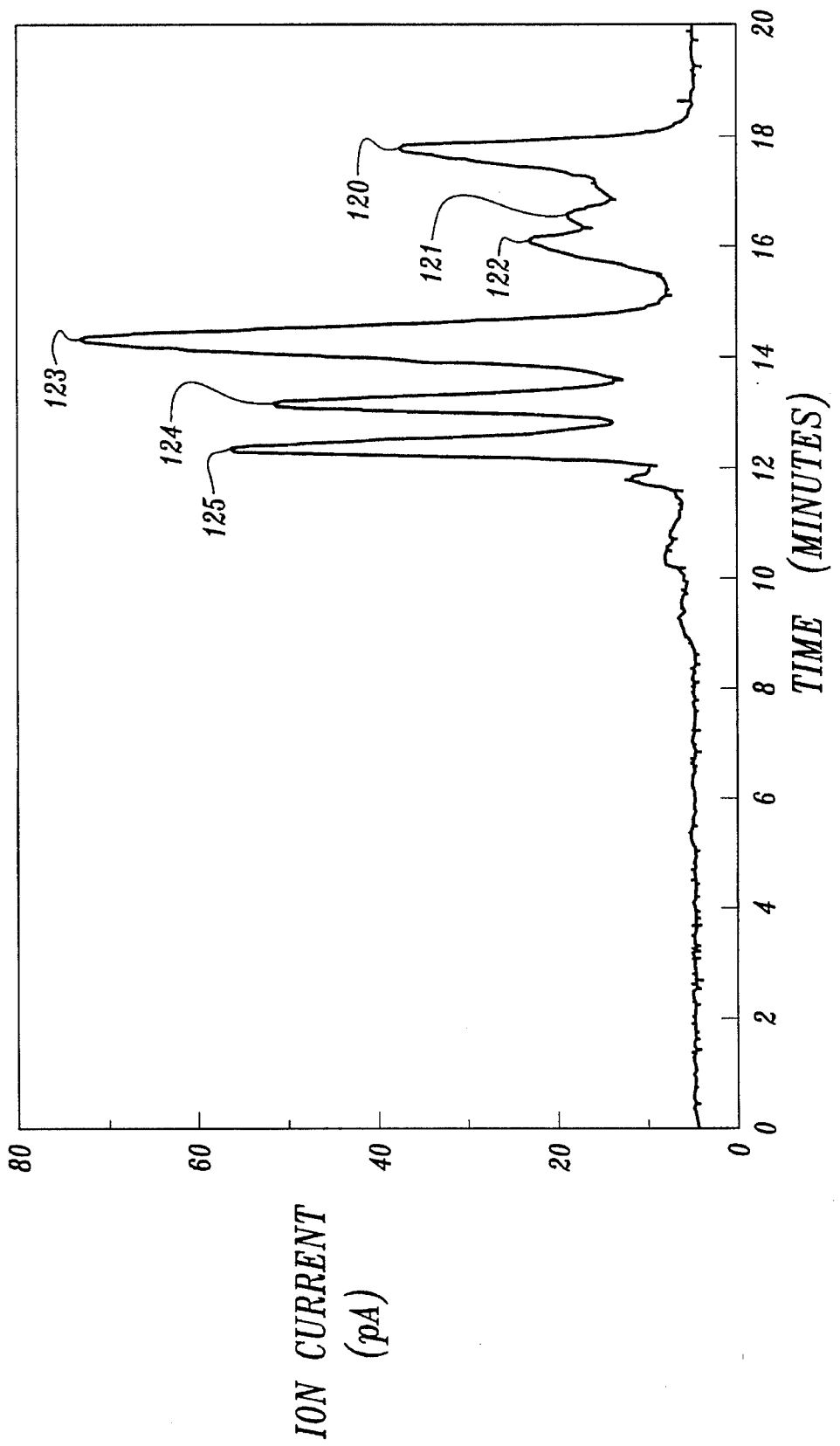
FIG. 5 is a graphical representation of an elution profile derived from the separation of ions of various sizes that was achieved by the instant invention.

Now referring to FIG. 5, based on identification by simultaneous mass spectrometric analysis, the order of analyte elution is: lysozyme 120, myoglobin 121, carbonic anhydrase 122, ubiquitin 123, lactalbumin 124, and somatostatin 125.

The observation which is directly pertinent to this detection scheme is that only the ion beam 3 originating from the ionized analyte is detected on the detection electrode. While the details of this discrimination phenomenon are still under investigation, it is most likely due to a combination of the greater collimation of heavier species of ions 3 upon expansion from the high pressure ion source 5 and their lower diffusion rates compared to smaller species of ions 3.

An additional factor which may contribute to this discrimination effect, is the selective loss of smaller ions by diffusion to the capillary walls. After formation from the electrosprayed droplets, the smaller ions will have higher diffusion rates and will be selectively lost by neutralization at the metal capillary surface of the desolvation capillary 11; it is also possible that larger multiply charged species that do diffuse to the walls will only loose part of their charge, and still be detected. If this mechanism were significant, it could provide the basis for an even simpler ion current detection device based upon the discrimination obtained in transport through longer capillaries.

Other Embodiments

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. An apparatus for detection of ions resulting from the separation of components in solution comprising:
    (a) a high pressure ion source;
    (b) a desolvation capillary having a receiving tip attached to a medium voltage source;
    (c) at least one collimating aperture through a collimating plate connected to a voltage source;

(d) at least one vacuum chamber housing said collimating aperture and said desolvation capillary wherein;
  (i) said ions originate from said high pressure ion source, and proceed through said desolvation capillary, then through said collimating aperture, and impinge upon an ion collector plate;
  (ii) said impingement producing a signal that is transmitted to;
(e) an ammeter;
whereby said ammeter indicates a temporal distribution that is proportional to a relative analyte abundance.

2. An apparatus for detection of ions resulting from the separation of components in solution comprising:
(a) a high pressure ion source;
(b) a desolvation capillary having a receiving tip attached to a medium voltage source;
(c) at least one skimmer assembly, said skimmer assembly having, a skimmer cone having a cone aperture, said skimmer cone biased to a predetermined voltage,
(d) at least one vacuum chamber housing said skimmer assembly and said desolvation capillary;
(e) a second vacuum chamber housing an ion collector plate, said ion collector plate connected to a ammeter lead, said ammeter lead connected to an ammeter, wherein;
  (i) said ions originate from said high pressure ion source, and proceed through said desolvation capillary, then through a collimating aperture, and impinge upon said ion collector plate;
  (ii) said impingement producing a signal that is transmitted to;
(f) said ammeter;
whereby said ammeter indicates a temporal distribution that is proportional to analyte charge state and abundance.

3. The apparatus in claim 2 wherein said skimmer assembly has a multiplicity of skimmer cone assemblies and at least one lens assembly.

4. The apparatus in claim 2 having two skimmer cones.

5. The apparatus in claim 2 wherein said ion collection plate is a shutter assembly.

6. The apparatus in claim 5 wherein said shutter assembly has a shutter body with a shutter aperture that is alternately closed or opened by an operating arm.

7. The apparatus in claim 2 wherein the desolvation capillary is heated.

8. An apparatus for detection of ions resulting from the separation of components in a solution comprising:
(a) a high pressure ion source;
(b) a desolvation capillary having a receiving tip attached to a medium voltage source;
(c) at least one skimmer assembly, said skimmer assembly having, a skimmer cone having a cone aperture, said skimmer cone being biased to a predetermined voltage, a lens having a lens aperture, said lens being biased to a predetermined voltage;
(d) at least one vacuum chamber housing said skimmer assembly and said desolvation capillary;
(e) a second vacuum chamber housing an ion collector plate, said ion collector plate being connected to a ammeter lead, said ammeter lead being connected to an ammeter, wherein;
  (i) said ions originate from said high pressure ion source, and proceed through said desolvation capillary, then through a collimating aperture, and impinge upon an ion collector plate;
  (ii) said impingement producing a signal that is transmitted to;
(f) said ammeter;
whereby said ammeter indicates a temporal distribution that is proportional to analyte charge state and abundance.

9. The apparatus in claim 3 wherein said ion collection plate is a shutter assembly.

* * * * *